United States Patent [19]
Niederhofer et al.

[11] Patent Number: 5,554,146
[45] Date of Patent: Sep. 10, 1996

[54] MECHANICAL FASTENER FOR DISPOSABLE ARTICLE

[75] Inventors: Laura S. Niederhofer, St. Paul; Leigh E. Wood, Woodbury; Stephen P. Polski, Shoreview, all of Minn.

[73] Assignee: Minnesota Mining and Manufacturing Company, St. Paul, Minn.

[21] Appl. No.: 239,042

[22] Filed: May 6, 1994

[51] Int. Cl.⁶ .................................................. A61F 13/15
[52] U.S. Cl. .................................... 604/391; 24/442
[58] Field of Search .................. 604/385.1, 386–391; 2/400; 24/442, 452, 306

[56] References Cited

U.S. PATENT DOCUMENTS

| | | | |
|---|---|---|---|
| 3,610,244 | 10/1969 | Jones | 128/287 |
| 4,699,622 | 10/1987 | Toussant et al. | 604/389 |
| 5,019,065 | 5/1991 | Scripps | 604/391 |
| 5,019,072 | 5/1991 | Polski | 604/389 |
| 5,066,289 | 11/1991 | Polski | 604/389 |
| 5,176,670 | 1/1993 | Roessler et al. | 604/391 |
| 5,256,231 | 10/1993 | Gorman et al. | 156/178 |
| 5,401,275 | 3/1995 | Flug et al. | 604/391 |

FOREIGN PATENT DOCUMENTS

| | | | |
|---|---|---|---|
| 0679196 | 2/1964 | Canada | 604/391 |
| 0529681A1 | 3/1993 | European Pat. Off. | |

*Primary Examiner*—Robert A. H. Clarke
*Attorney, Agent, or Firm*—Gary L. Griswold; Walter N. Kirn; William J. Bond

[57] ABSTRACT

A mechanical fastening system for a diaper or like disposable garment of a male mechanical fastening tab (e.g., a hook-type fastener) attached to a corner or edge region of the garment with a mating fibrous web on an opposing corner or edge region. The male mechanical fastening tab creates two areas of attachment, an outward portion extending beyond the first corner or edge region and an inward area extending inward of the first corner or edge region, where both areas of attachment engage the fibrous web on the opposing corner or edge. The male mechanical fastening tab with the fibrous web creates a secure non-rotational attachment using a single fastening tab.

46 Claims, 3 Drawing Sheets

MECHANICAL FASTENER FOR DISPOSABLE ARTICLE

BACKGROUND AND FIELD OF THE INVENTION

The invention is concerned with disposable diapers and incontinent articles having refastenable mechanical closures and is specifically concerned with improvements in fit and closure stability.

Conventional commercial disposable diapers and adult incontinent products typically use pressure-sensitive adhesive (PSA) fastening tabs to close the diaper. Typically these PSA fastening tabs extend beyond the side edge of the diaper at a first ear or corner portion and attach to an opposing ear or corner portion as the opposing ears are overlapped in placing the diaper around the user. As such, the PSA fastening tab is permanently attached at a "manufacturers end" to one ear directly adjacent the side edge of that ear and refastenably attached at an inward location on the opposing ear or corner portion by a free end of the PSA fastening tab.

An improvement on the above basic adhesive closure system is the inclusion of a secondary pair of closure elements, which also engage when the two opposing ears are overlapped. This so-called "inner fastening means" is generally formed by placing a fastening element on an inner face the first ear, which engages with a corresponding or matched fastening surface or element on the outer face of the opposing ear. In this manner, the ears are directly secured to each other at their overlapping faces as well as by the conventional PSA fastening tab. The use of secondary closure elements is proposed in U.S. Pat. No. 4,699,622, which describes an elasticated diaper using an outer fastening tab and an inner fastening means. The conventional outer fastening tab extends from the longitudinal side edge at a first corner of the diaper. The inner fastening means is described as potentially including "VELCRO" strips, adhesive patches, buttons or snaps, but is preferably a mechanical fastening element placed on the outer face of the second opposing corner that engages with the topsheet nonwoven forming the inner face of the first corner. Specific improvements to the arrangement in U.S. Pat. No. 4,699,622 are described in U.S. Pat. No. 5,019,072, where the inner fastening means is a specifically described pair of overlapping cohesive or peelable adhesive patches on both the first corners or ears and the second opposing corners or ears, which patches are positioned such that they overlap when the opposing ears or corners of the diaper are overlapped when attaching the outer adhesive fastening tabs. U.S. Pat. No. 5,066,289 describes an improvement of the preferred design in U.S. Pat. No. 4,699,622, by providing a specific foraminous substrate on the inner face of the first corner for use as the release tape for the outer pressure-sensitive adhesive fastening tab. This foraminous release tape increases the attachment effectiveness of a male mechanical inner fastening means located on the second opposing ear of the diaper. U.S. Pat. No. 3,610,244 also proposes secondary closure elements. The patent describes using a conventional PSA fastening tab on a first corner of the diaper. In addition the inner face of this first corner contacts a PSA patch located on the outside face of the second opposing corner when the two opposing corners are attached in an overlapping relation with the conventional PSA fastening tab. The four points of adhesive attachment are described as providing more secure fit for active babies.

Although use of a secondary closure on the overlapping corners provides improved fit by inhibiting rotational shifting of the overlapping corners of the diaper, each with respect to each other, either from wearer movement or forces from the elasticized portions of the diaper, these systems are often exceedingly complicated to manufacture, requiring up to eight separate adhesive or mechanical fastening elements per diaper.

SUMMARY OF THE INVENTION

The invention is directed to a mechanical, or hook and loop, closure system for a disposable garment, specifically, disposable incontinent products such as a diaper. The male mechanical fastening tab has a first end extending beyond the outer side edge of a first ear or corner, and a second end extending inward of the outer side edge of the first corner. Both ends of the mechanical fastening tab are engagable with a mating, woven, stichbonded, knitted or the like, or nonwoven web on the second opposing ear corner, the mechanical fastening tabs two ends serve as an outer mechanical fastening tab element and an inner panel face-to-panel face fastening element. The two mechanical fastening elements provided by the invention closure system provide improved fit and closure stability using a simple and easy to apply single mechanical fastening tab.

DETAILED DESCRIPTION OF THE INVENTION

The following detailed description of the invention is made with respect to certain preferred embodiments of the invention closure system on a conventional disposable diaper chassis. However, it would be apparent to one skilled in the art that the preferred embodiments of the invention mechanical fastener closure systems would be applicable to other articles, such as hospital gowns, caps, incontinent garments, other diaper designs and the like.

Figure 1:
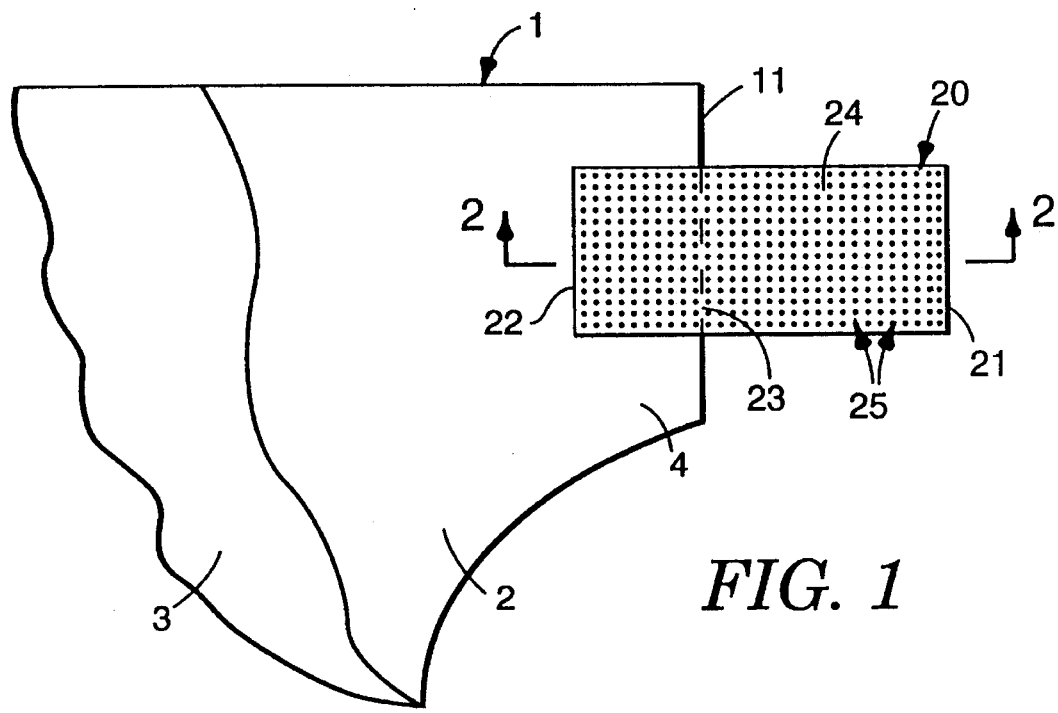
FIG. 1 is a cut-away plan view of a first embodiment of the invention showing a male mechanical fastening tab placed on a side corner of a diaper.
Figure 2:
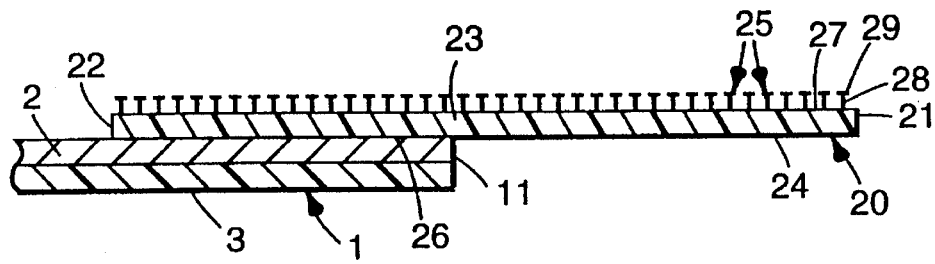
FIG. 2 is a sectional side view of the FIG. 1 embodiment.
Figure 3:
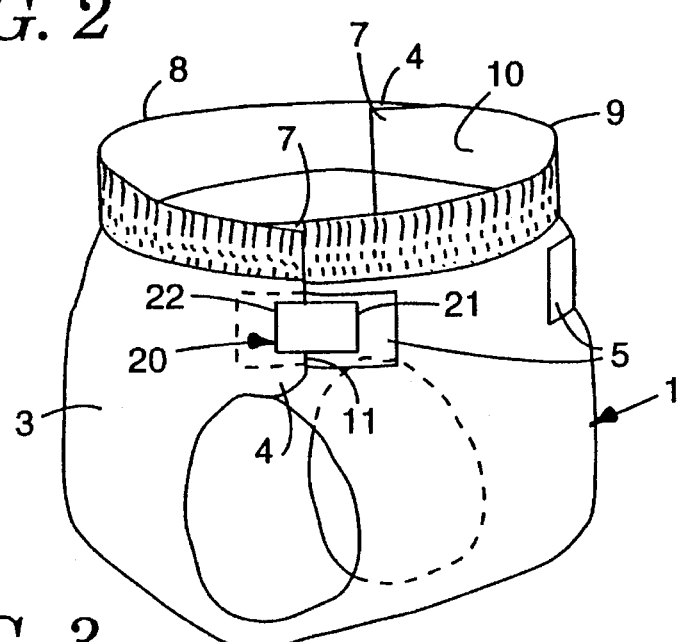
FIG. 3 is a perspective view of a disposable diaper with the mechanical fastener closure system shown in FIGS. 1 and 2.

Referring to FIGS. 1–3, a first preferred embodiment of the invention mechanical closure system is disclosed with respect to a conventional diaper chassis absorbent body (1). The diaper absorbent body (1) comprises a liquid-permeable topsheet (2) and a liquid-impermeable backsheet (3), between which is a conventional absorbent pad (not shown).

At least a first corner (4) at a first end (8) of the diaper chassis (1) has a mechanical fastening tab (20) designed to adhere to a mating mechanical fastening element (5), and/or the backsheet (3), at a second end (9) of the diaper chassis (1). When the diaper is worn, i.e. when the invention mechanical fastening closure system is in use, the first corners (4) at the first end (8) of the disposable diaper overlap with corresponding second opposing corners (7) at the opposing end (9) of the diaper chassis, so that the two opposing corners (4) and (7) have mutually abutting faces. In the conventional diaper chassis design of FIG. 3, where both first corners (4) are placed over both corresponding second opposing corners (7) and the mechanical fastening elements (20) engage with the backsheet (3) and/or the mating mechanical fastening element (5), the diaper chassis defines a waist opening (10) encircling the torso of the wearer.

The liquid-permeable topsheet (2) would comprise any conventional material known for this use, including spunbond webs, meltblown webs, carded webs, and the like, which conventionally are formed of thermoplastic and hydrophobic polymer fibers, such as polyolefin or polyester fibers.

The backsheet (3) is a liquid-impermeable web or film and conventionally is a thin polymer film, such as a thin polyolefin film, i.e., polyethylene or polypropylene, mixtures, blends or coextruded versions, generally less than 2 mils thick. Liquid-impermeable, but vapor-permeable microporous films may also be used to form the backsheet (3).

In a preferred embodiment, the backsheet (3) comprises a laminate of a liquid-impermeable film with a nonwoven or woven, stitchbonded, knitted or the like, fibrous web, which fibrous web is engagable with the mechanical fastening structures (25) on the mechanical fastening tab (20). Suitably, this laminate can be formed by adhesive lamination, pattern welding, i.e., sonic or heat or cold welding, or direct formation of the web on all or part of the liquid-impermeable film. The fibrous web would face outward so as to be engagable with the mechanical fastening tab.

Preferably, a fibrous web, provided as an outer layer of a backsheet laminate (3) or a mating mechanical element (5), will have sufficient fiber loft, fiber spacing, and fiber size to allow penetration by the mechanical fastening structures (25) of tab (20) but sufficient fiber density and size so that a substantial portion of the mechanical fastening structures (25) engage fibers of the web.

Specifically, the backsheet (3), or mating mechanical fastening element (5), can be a laminate of liquid-impermeable film and a loop fabric, such as those described in U.S. Pat. No. 5,176,670, or any other conventional loop fabric. The loop fabric can be any conventional fibrous loop, including nonwovens, fabric, provided with suitable backing(s) as required. The fabrics are formed of conventional fibers including nylon, polyester, polypropylene, or other like synthetic or natural fibers. A preferred loop fabric would be such as described in U.S. Pat. No. 5,256,231, where corrugated oriented fibers are extrusion bonded to a thermoplastic backing, "SCOTCH-MATE" loop fabrics (available from 3M Company), or "MILLILOCK" (a stichbonded loop fabric available from Milliken Company).

The fibrous web, including loop fabrics, may also be extrusion laminated to a liquid-impermeable barrier layer on one face of the fibrous web, which can then be used as the backsheet or mating mechanical fastening element (5) or further laminated to a film, a scrim, or the like, for added strength.

In the first embodiment of the invention closure system, shown in FIGS. 1 and 2, the mechanical fastening tab (20) is provided with male mechanical fastening structures (25), which can be any suitable fiber engaging shape. A general fiber engaging shape comprises an upstanding stem having a base stem portion (28) and a distal fiber engaging element (29) at the outermost end of the stem (25). The base stem portion (28) is generally narrower than the fiber engaging element (29) over its full length and has no outward protrusions or fiber engaging structures. Generally the stem portion (28) has straight sides or tapers inwardly from the fastening tab (20) face to the fiber engaging element (29). The fiber engaging element (29) can be in the shape of a mushroom, circular disk, J-hook, bilobal(T-shaped), multilobal or any other suitable shape capable of engaging fibers. The male mechanical fastening structure from stem base (28) to outermost surface of the fiber engaging element (29), generally is at least 75 microns high, preferably 200 to 400 microns high. Suitable materials for forming the hook include thermoplastic polymers, such as polyester, polyolefins, nylons, and the like.

The mechanical fastening tab (20) is provided with an outward end portion (21) extending beyond the edge (11) of the corner (4) and an inward end portion (22) extending into the diaper chassis (1) corner (4), which two end portions (21 and 22) are separated by a transition region (23). Both the inward end portion (22) and the outward end portion (21) are capable of engaging the fibrous mating mechanical fastening element(s) (5) and/or an outer fibrous web of a backsheet laminate (3). The outward end portion (21) provides a convenient grippable attachment for easy placement and removal of the male mechanical fastening tab 20. The inward end portion (22) when engaged with backsheet (3) or mating fastening elements (5) limits rotational shifting of the opposing corners (4) and (7), each with respect to the other, during normal wear and usage.

In the embodiment of FIGS. 1 and 2, the mechanical fastening tab (20) is attached to the diaper chassis (1) at a face (26) opposite the face (27) containing the male mechanical fastening structures (25). The inward end portion (22) can be attached to the diaper chassis (1) by any method which does not substantially destroy or impair the fiber engaging function of the male mechanical fastening structures (25) on the inward end portion (22), which includes adhesive bonding, intermittent or spot welding (sonic, heat or cold welding, or the like) or the like.

Fastening tab backing (24) is preferably an integral or separate thermoplastic film formed of the same thermoplastic polymer as a male mechanical fastening structures (25), however backing (24) could be a fibrous web structure where the male mechanical fastening structures are formed by knitting or a like operation. Other backings and substrates can also be used including conventional thermoplastic films, fibrous webs or the like.

Figure 4:
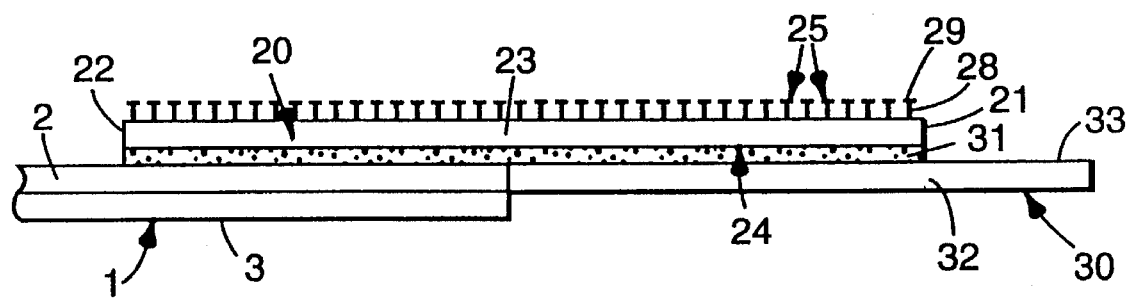
FIG. 4 is a side view of a second embodiment of the invention.

FIG. 4 illustrates an alternative embodiment of the invention mechanical fastening closure system, where like numerals indicate like elements. In this embodiment, the mechanical fastening tab (20) is attached to a backing substrate (32), which is provided with an extending fingerlift portion (33), free of mechanical fastening structures or adhesives. The fingerlift portion (33) allows the fastening tab/backing substrate laminate (30) to be gripped for removal. Backing structure (32) can be any substrate provided it is flexible, and would conventionally be a thermoplastic film or fibrous web. The use of backing (32) allows mechanical fastening tab (20) to be applied via a continuous pressure-sensitive adhesive layer (31). For example the mechanical fastening tab (20) can be cut from a continuous pressure-sensitive adhesive coated tape. The tape could be continuously laminated to the backing (32) and then cut into individual mechanical fastening tab laminates (30) and adhered to the diaper chassis (1) without on-line adhesive coating or welding of the inward end portion (22) to the diaper chassis (1).

Figure 5:
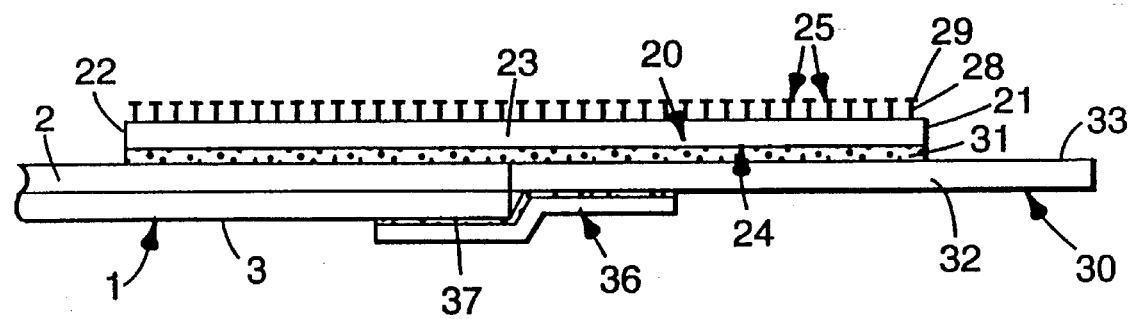
FIG. 5 is a side cut-away view of a third embodiment of the invention.
Figure 6:
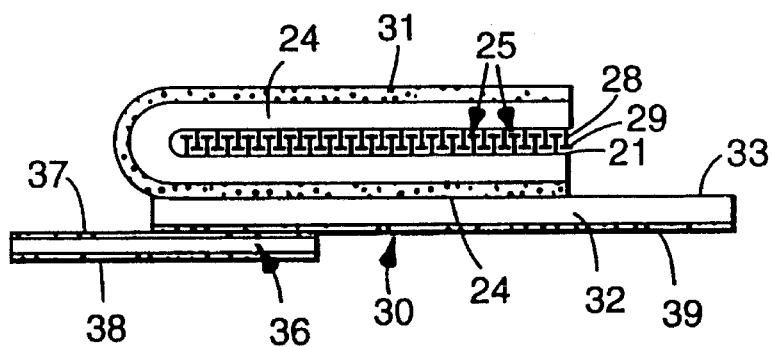
FIG. 6 is a side view of the FIG. 5 embodiment prior to application to the diaper.

FIG. 5 illustrates an alternative embodiment of the FIG. 4 structure wherein an additional reinforcing element (36) is provided so as to provide more secure attachment of the mechanical fastening tab (20) outward end portion (21), to the diaper chassis (1). This reinforcing element (36) would generally be a PSA tape adhered to the diaper chassis at one end and the mechanical fastening element (20) outer end (21) at the other end, either directly or through the backing (32) as shown in FIG. 5. The structure shown in FIG. 5 can be assembled from separate individual tapes or films on a diaper line or provided as a prelaminate tape structure, such as shown in FIG. 6. With the FIG. 6 prelaminate tape structure the reinforcing element (36) and the backing (32) would be preferably provided with low adhesion backsize or release coatings (38) and (39) to allow the prelaminate structure to be unrolled from a continuous roll as a tape without blocking of the adhesive layers (37) and (31). The reinforcing element (36) could be used with other embodiments of the invention as well, such as the embodiment of FIG. 1.

Figure 7:
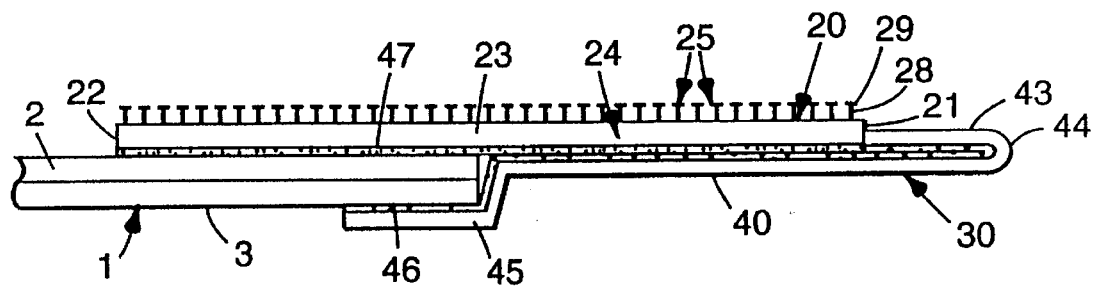
FIG. 7 is a side cut-away view of a fourth embodiment of the invention.
Figure 8:
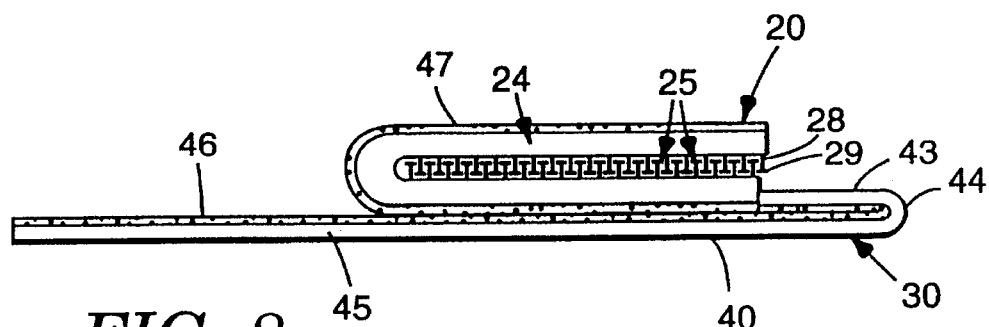
FIG. 8 is a side view of the FIG. 7 embodiment prior to application to a diaper.

The FIGS. 7 and 8 embodiment in a variation of the FIGS. 5 and 6 embodiment where the backing substrate (40) extends into the diaper chassis at an end (45), providing the mechanical fastening element (20) with two points of permanent attachment to the diaper chassis, such as in the FIGS. 5 and 6 embodiment, without a separate reinforcing element (36). An optional variation of this embodiment, as well as the embodiments of FIGS. 4–6, and like structures, is that a finger lift portion (43) is provided by folding over an end of a backing (40), providing a softer folded edge (44). The FIG. 7 mechanical fastening structure can be assembled from separate films or tapes on the diaper line or cut from a prelaminate tape structure, as shown in FIG. 8, where the pressure-sensitive adhesive layers (46) and (47) provide for attachment to the diaper, as shown in FIG. 7. The backing substrate (40), in the FIG. 8 tape prelaminate, would conventionally be provided with a release or low adhesion backsize coating (not shown).

Figure 9:
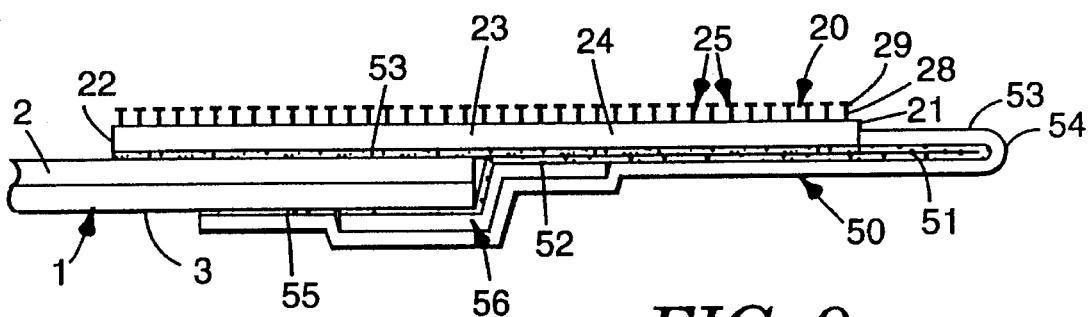
FIG. 9 is a side cut-away view of a fifth embodiment of the invention.

In the embodiments shown in FIG. 9, the backing layer (50) of the FIG. 7 embodiment is provided with an additional reinforcement tape (56), so as to provide additional reinforcement for attachment of the mechanical fastening element (20). This design is desirable where the backing (50) is a web having low tensile strength, such as a lightly consolidated or point bonded nonwoven web, like a spunbond or meltblown web.

Figure 10:
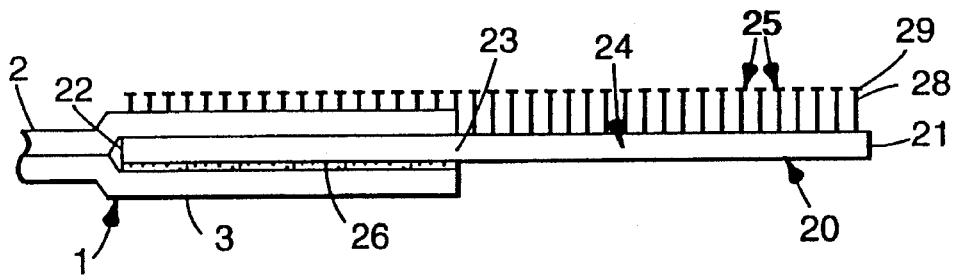
FIG. 10 is a side cut-away view of a sixth embodiment of the invention.

FIG. 10 illustrates an alternative method for attaching the inward end portion (22) of the mechanical fastening element (20) to the diaper chassis (1). In this instance, the inward end portion (22) is sandwiched between the liquid-impermeable backsheet (3) and the liquid-permeable topsheet (2) where the topsheet has a sufficiently open structure such that the male mechanical fastening structures (25) can protrude outwardly therefrom sufficiently to engage fibers of a fibrous web on the mating mechanical fastening element (5) or the backsheet (3), as described above. In this embodiment, preferably the male mechanical fastening structures (25) are somewhat larger and would conventionally extend at least about 150 microns from the backing (24). This embodiment provides for very secure attachment of the mechanical fastening element (20) to the diaper chassis using the male mechanical fastening structures (25) at the inward end portion (22) to mechanically engage with the liquid-permeable topsheet. Additional attachment of the opposing face (26) of the fastening tab (20) to the backsheet (3) can be accomplished as described above using adhesive, welding or the like. This form of attachment can be used with any of the above-described embodiments, in conjunction with the use of separate reinforcing tape, or a substrate attached to the outer face of the backsheet (3) and/or face (26) of the fastening tab (20).

Generally, the inward end portion (22) is shorter in the length direction than the outward end portion (21), allowing the outward end portion (21) to extend beyond the inward end portion (22) when folded towards the topsheet (2). This allows a certain portion of the mechanical fastening structures (25) to mechanically engage with fibers of a topsheet (2) prior to use, keeping the outward end portion (21) folded. However, this is not as critical in the attachment method of FIG. 10 in that the mechanical fastening structures (25) on the outward end (21) can also engage with the fibers of the topsheet (2) in the area where topsheet (2) is attached to the inward end portion (22). The mechanical fastening structures (25) can also be self-engaging.

During use, both the outward end, and inward end portions, (21) and (22), respectively, engage with a fibrous web of the mating mechanical fastening element (5) and/or a fibrous web, laminated or otherwise formed, on the liquid-impermeable backsheet (3), such that both the outward end portion (21) and the inward end portion (22) are fully engaged, thus allowing secure non-rotational attachment between the corners (4) and (7). Both shear and peel resistance can be provided by suitable selection of the fibrous web fibers or structures (25) of the male mechanical fastening tab (20). Generally, the shear resistance provided by the inward fastening end portion (21) of the fastening tab (20) should be greater than 500 grams, which can generally be provided by a mechanical fastening tab having a width of greater than about 1.5 cm, preferably 2 to 5 cm, and a length of the inward end portion of from 1 to 3 cm. Generally, the outward portion (22) extends at least 1 cm beyond the side edge of the corner portion (4), preferably 3 to 6 cm.

Other embodiments of the invention will be apparent to those skilled in the art from a consideration of the specification or practice of the invention disclosed herein. It is intended that the specification and specifically described embodiments be considered as exemplary only, with the true scope and spirit of the invention being indicated by the following claims.

What is claimed is:

1. A closure system on a disposable absorbent article comprising a disposable absorbent article with at least two corner portions each of said corner portions having a liquid-permeable inner layer formed from a nonwoven fibrous web and a liquid-impermeable outer layer, and a mechanical fastening tab adjacent a first edge of a first of said two corner portions, the liquid-impermeable outer layer at a second opposing corner of said two corner portions having a first fibrous web on an outer surface of said liquid-impermeable outer layer engageable with said mechanical fastening tab, said mechanical fastening tab having a first face and a second face, at least said first face having male mechanical fastening structures engageable with said first fibrous web, a first inward end portion of said mechanical fastening tab located adjacent said liquid-impermeable inner layer and engaged therewith, and an outward end portion of said mechanical fastening tab extending outward of said first corner portion at said first edge wherein both said inward end potion and outward end portion have said male mechanical fastening structures such that both end portions are engageable with said first fibrous web wherein said inward end portion mechanically engages said nonwoven fibrous web inner layer by said male mechanical fastening structures such that the male mechanical fastening structures project through said nonwoven fibrous web and are engageable with said first fibrous web.

2. The closure system of claim 1 wherein said outward end portion is longer than said inward end portion, such that when said outward end portion is folded onto said inward end portion, a section of said outward end portion having said male mechanical fastening structures is engageable with said nonwoven fibrous web inner layer.

3. The closure system of claim 1 wherein said inward end portion is further adhesively bonded to said liquid-impermeable outer layer at said second face of said mechanical fastening tab.

4. The closure system of claim 1 wherein the nonwoven fibrous web inner layer comprises a spunbond web of thermoplastic fiber.

5. The closure system of claim 1 wherein the male mechanical fastening structures are at least 75 microns high from the stem base to the outermost surface of the fiber engaging element.

6. The closure system of claim 1 wherein the mechanical fastening tab has a length of from 4 cm to 9 cm and a width of greater than 1.5 cm.

7. A closure system on a disposable absorbent article comprising a disposable absorbent article with at least two corner portions each of said corner portions having a liquid-permeable inner layer of a spunbond web of thermoplastic fibers and a liquid-impermeable outer layer, and a mechanical fastening tab adjacent a first edge of a first of said two corner portions, the liquid-impermeable outer layer at a second opposing corner of said two corner portions having a first fibrous web on an outer surface of said liquid-impermeable outer layer engageable with said mechanical fastening tab, said mechanical fastening tab having a first face and a second face, at least said first face having male mechanical fastening structures engageable with said first fibrous web, a first inward end portion of said mechanical fastening tab located adjacent said liquid-impermeable inner layer and engaged therewith, and an outward end portion of said mechanical fastening tab extending outward of said first corner portion at said first edge wherein both said inward end potion and outward end portion have said male mechanical fastening structures such that both end portions are engageable with said first fibrous web.

8. The closure system of claim 7 wherein said outward end portion is longer than said inward end portion, such that when said outward end portion is folded onto said inward end portion, a section of said outward end portion having said male mechanical fastening structures is engageable with said nonwoven fibrous web inner layer.

9. The closure system of claim 7 wherein said liquid-impermeable outer layer comprises a liquid impermeable thermoplastic film.

10. The closure system of claim 9 wherein said first fibrous web comprises a patch of fibrous web material attached to said liquid-impermeable thermoplastic film at least in said second opposing corner.

11. The closure system of claim 9 wherein the liquid-impermeable thermoplastic film comprises a polyolefin film less than 2 mils (51 microns) thick.

12. The closure system of claim 7 wherein said inward end portion mechanically engages said nonwoven fibrous web inner layer by said male mechanical fastening structures such that the male mechanical fastening structures project through said nonwoven fibrous web and are engageable with said first fibrous web.

13. The closure system of claim 7 wherein the male mechanical fastening structures comprise upstanding stems having fiber engaging elements at the outermost ends of the stems.

14. The closure system of claim 13 wherein the male mechanical fastening structures are at least 75 microns high from the stem base to the outermost surface of the fiber engaging element.

15. The closure system of claim 9 wherein the mechanical fastening tab is provided with a continuous pressure-sensitive adhesive coating in both the inward end portion and the outward end portion on said second face of said mechanical fastening tab, and wherein said outward end portion is attached to a backing substrate and said inward end portion is attached to said first corner portion by said pressure-sensitive adhesive layer.

16. The closure system of claim 15 further comprising a reinforcing element attached at an inward end to said liquid-impermeable outer layer and at an outward end to said mechanical fastening tab outward end.

17. The closure system of claim 15 wherein said backing substrate is further attached to the outer face of said liquid-impermeable outer layer.

18. The closure system of claim 7 wherein said inward end portion pressure-sensitive adhesive layer is attached to said liquid-permeable inner layer.

19. The closure system of claim 7 wherein said inward end portion pressure-sensitive adhesive layer is attached to said liquid-impermeable outer layer.

20. A closure system on a disposable absorbent article comprising a disposable absorbent article with at least two corner portions each of said corner portions having a liquid-permeable inner layer and a liquid-impermeable outer layer, and a mechanical fastening tab adjacent a first edge of a first of said two corner portions, the liquid-impermeable outer layer at a second opposing corner of said two corner portions having a first fibrous web on an outer surface of said liquid-impermeable outer layer engageable with said mechanical fastening tab, said mechanical fastening tab having a first face and a second face, at least said first face having male mechanical fastening structures engageable with said first fibrous web, a first inward end portion of said mechanical fastening tab located adjacent said liquid-impermeable inner layer and engaged therewith, and an outward end portion of said mechanical fastening tab extending outward of said first corner portion at said first edge wherein both said inward end potion and outward end portion have said male mechanical fastening structure such that both end portions are engageable with said first fibrous web wherein the mechanical fastening tab is provided with a continuous pressure-sensitive adhesive coating in both the inward end portion and the outward end portion on said second face of said mechanical fastening tab, and wherein said outward end portion is attached to a backing substrate and said inward end portion is attached to said first corner portion by said pressure-sensitive adhesive layer.

21. The closure system of claim 20 wherein said liquid permeable inner layer is a nonwoven fibrous web and said liquid-impermeable outer layer comprises a liquid impermeable thermoplastic film.

22. The closure system of claim 20 wherein said outward end portion is longer than said inward end portion, such that when said outward end portion is folded onto said inward end portion, a section of said outward end portion having said male mechanical fastening structures is engageable with said nonwoven fibrous web inner layer.

23. The closure system of claim 20 wherein said first fibrous web comprises a nonwoven fibrous web or a woven, stitchbonded or knitted fabric.

24. The closure system of claim 20 wherein said inward end portion mechanically engages said nonwoven fibrous web inner layer by said male mechanical fastening structures such that the male mechanical fastening structures project through said nonwoven fibrous web and are engageable with said first fibrous web.

25. The closure system of claim 20 wherein the male mechanical fastening structures comprise upstanding stems having fiber engaging elements at the outermost ends of the stems.

26. The closure system of claim 20 wherein the male mechanical fastening structures are at least 75 microns high from the stem base to the outermost surface of the fiber engaging element.

27. The closure system of claim 20 wherein said inward end portion pressure-sensitive adhesive layer is attached to said liquid-permeable inner layer.

28. The closure system of claim 20 wherein said inward end portion pressure-sensitive adhesive layer is attached to said liquid-impermeable outer layer.

29. The closure system of claim 20 further comprising a reinforcing element attached at an inward end to said liquid-impermeable outer layer and at an outward end to said backing substrate on said mechanical fastening tab outward end.

30. The closure system of claim 20 wherein said backing substrate is further attached to the outer face of said liquid-impermeable outer layer.

31. The closure system of claim 20 further comprising a reinforcing element attached at an inward end to said outer face of said liquid-impermeable outer layer and at an outward end to said mechanical fastening tab outward end.

32. The closure system of claim 31 wherein said backing substrate comprises a nonwoven web.

33. A closure system on a disposable absorbent article comprising a disposable absorbent article with at least two corner portions each of said corner portions having a liquid-permeable inner layer and a liquid-impermeable outer layer formed of a polyolefin film with a thickness of less than 2 mils (51 microns), and a mechanical fastening tab adjacent a first edge of a first of said two corner portions, the liquid-impermeable outer layer at a second opposing corner of said two corner portions having a first fibrous web on an outer surface of said liquid-impermeable outer layer engageable with said mechanical fastening tab, said mechanical fastening tab having a first face and a second face, at least said first face having male mechanical fastening structures engageable with said first fibrous web, a first inward end portion of said mechanical fastening tab located adjacent said liquid-impermeable inner layer and engaged therewith, and an outward end portion of said mechanical fastening tab extending outward of said first corner portion at said first edge wherein both said inward end potion and outward end portion have said male mechanical fastening structures such that both end portions are engageable with said first fibrous web.

34. The closure system of claim 33 wherein said liquid permeable inner layer is a nonwoven fibrous web.

35. The closure system of claim 34 wherein said outward end portion is longer than said inward end portion, such that when said outward end portion is folded onto said inward end portion, a section of said outward end portion having said male mechanical fastening structures is engageable with said nonwoven fibrous web inner layer.

36. The closure system of claim 33 wherein said inward end portion is adhesively bonded to said liquid permeable inner layer at said second face of said mechanical fastening tab.

37. The closure system of claim 33 wherein said inward end portion is point bonded to said liquid-permeable inner layer.

38. The closure system of claim 33 wherein the mechanical fastening tab is provided with a continuous pressure-sensitive adhesive coating in both the inward end portion and the outward end portion on said second face of said mechanical fastening tab, and wherein said outward end portion is attached to a backing substrate and said inward end portion is attached to said first corner portion by said pressure-sensitive adhesive layer.

39. The closure system of claim 38 wherein said inward end portion pressure-sensitive adhesive layer is attached to said liquid-permeable inner layer.

40. The closure system of claim 38 wherein said inward end portion pressure-sensitive adhesive layer is attached to said liquid-impermeable outer layer.

41. A closure system on a disposable absorbent article comprising a disposable absorbent article with at least two corner portions each of said corner portions having a liquid-permeable inner layer and a liquid-impermeable outer layer, and a mechanical fastening tab adjacent a first edge of a first of said two corner portions, the liquid-impermeable outer layer at a second opposing corner of said two corner portions having a first fibrous web on an outer surface of said liquid-impermeable outer layer engageable with said mechanical fastening tab, said mechanical fastening tab having a first face and a second face, at least said first face having male mechanical fastening structures engageable with said first fibrous web, a first inward end portion of said mechanical fastening tab located adjacent said liquid-impermeable inner layer and engaged therewith, and an outward end portion of said mechanical fastening tab extending outward of said first corner portion at said first edge and a reinforcing element attached at an inward end to said liquid impermeable outer layer and at an outward end to said mechanical fastening tab outward end portion wherein both said inward end potion and outward end portion have said male mechanical fastening structures such that both end portions are engageable with said first fibrous web.

42. The closure system of claim 41 wherein said liquid permeable inner layer is a nonwoven fibrous web and said liquid impermeable outer layer comprises a liquid impermeable thermoplastic web.

43. The closure system of claim 42 wherein said outward end portion is longer than said inward end portion, such that when said outward end portion is folded onto said inward end portion, a section of said outward end portion having said male mechanical fastening structures is engageable with said nonwoven fibrous web inner layer.

44. The closure system of claim 41 wherein said inward end portion is adhesively bonded to said liquid-permeable inner layer at said second face of said mechanical fastening tab.

45. The closure system of claim 41 wherein said inward end portion mechanically engages said nonwoven fibrous web inner layer by said male mechanical fastening structures such that the male mechanical fastening structures project through said nonwoven fibrous web and are engageable with said first fibrous web.

46. The closure system of claim 41 wherein the male mechanical fastening structures comprise upstanding stems having fiber engaging elements at the outermost ends of the stems wherein the male mechanical fastening structures are at least 75 microns high from the stem base to the outermost surface of the fiber engaging element.

* * * * *